(12) United States Patent
Basheer et al.

(10) Patent No.: US 9,075,037 B2
(45) Date of Patent: Jul. 7, 2015

(54) MICRO-SOLID PHASE EXTRACTION OF HALOACETIC ACIDS

(71) Applicants: KING FAHD UNIVERSITY OF PETROLEUM AND MINERALS, Dhahran (SA); KING ABDULAZIZ CITY FOR SCIENCE AND TECHNOLOGY, Riyadh (SA)

(72) Inventors: Chanbasha Basheer, Karimangalam (IN); Hakimu Nsubuga, Mbale (UG)

(73) Assignees: KING FAHD UNIVERSITY OF PETROLEUM AND MINERALS, Dhahran (SA); KING ABDULAZIZ CITY FOR SCIENCE AND TECHNOLOGY, Riyadh (SA)

( * ) Notice: Subject to any disclaimer, the term of this patent is extended or adjusted under 35 U.S.C. 154(b) by 0 days.

(21) Appl. No.: 14/024,526

(22) Filed: Sep. 11, 2013

(65) Prior Publication Data

US 2015/0068291 A1    Mar. 12, 2015

(51) Int. Cl.
- *G01N 33/18* (2006.01)
- *C02F 1/28* (2006.01)
- *G01N 30/00* (2006.01)

(52) U.S. Cl.
CPC .............. *G01N 33/18* (2013.01); *C02F 1/286* (2013.01); *G01N 2030/009* (2013.01)

(58) Field of Classification Search
CPC ........................................ G01N 30/02
USPC ................ 502/411; 252/62; 210/500.25
See application file for complete search history.

(56) References Cited

U.S. PATENT DOCUMENTS

| | | | |
|---|---|---|---|
| 4,619,911 A | 10/1986 | Goodwin et al. | |
| 4,680,059 A * | 7/1987 | Cook et al. | 106/705 |
| 6,500,238 B1 * | 12/2002 | Brandes et al. | 95/148 |
| 7,279,147 B2 | 10/2007 | Turkay et al. | |
| 2003/0186452 A1 * | 10/2003 | Shirahata et al. | 436/144 |
| 2005/0142649 A1 * | 6/2005 | Paul et al. | 435/188.5 |
| 2006/0175256 A1 * | 8/2006 | Masten et al. | 210/638 |
| 2013/0140239 A1 * | 6/2013 | Knighton et al. | 210/662 |
| 2014/0099727 A1 * | 4/2014 | Saini | 436/125 |

FOREIGN PATENT DOCUMENTS

| CN | 102565170 A | * | 7/2012 |
|---|---|---|---|
| WO | WO2012/158388 | * | 11/2012 |

OTHER PUBLICATIONS

Dang, Son Van at al., "Removal of Arsenic From Simulated Groundwater by Adsorption Using Iron-Modified Rice Husk Carbon", Journal of Water and Environment Technology, 2009, 7(2), 43-56.

Robert et al., "Determination of Haloacetic Acids in Aqueous Environments by Solid-Phase Extraction Followed by Ion-Pair Liquid Chromatography-Electrospray Ionization Mass Spectrometric Detection", Journal of Chromatography A, 2001, 938, 45-55.

* cited by examiner

*Primary Examiner* — Sally Merkling
(74) *Attorney, Agent, or Firm* — Richard C Litman

(57) ABSTRACT

The micro-solid phase extraction of haloacetic acids is a procedure that extracts haloacetic acids from aqueous solution using iron-modified rice husk silica as the stationary phase or sorbent. Rice husks provide an excellent source of silica. The sorbent is prepared by incinerating the husks to produce a powder that is treated with 1.0 M nitric acid for 24 hours to produce rice husk silica. The silica is washed with base, cetyltrimethylammonium bromide is added, and then titrated with a 10% $Fe^{3+}$ solution to pH 5, which forms a gel. The gel is aged, filtered, dried, and calcined to produce a nitrate-free iron-modified rice husk sorbent. The sorbent is then packaged in porous, heat-sealed polypropylene membrane envelopes and used for extraction of HAAs from water. The HAA analytes are desorbed by ultrasonication in methanol for analysis and quantification.

2 Claims, 3 Drawing Sheets

MICRO-SOLID PHASE EXTRACTION OF HALOACETIC ACIDS

BACKGROUND OF THE INVENTION

1. Field of the Invention

The present invention relates to solid phase extraction, and particularly to the micro-solid phase extraction of haloacetic acids from aqueous solution using an iron-modified rice husk sorbent for precise and selective determination of haloacetic acids (HAAs) in water matrices.

2. Description of the Related Art

Haloacetic acids (HAAs) are the second most prevalent group of disinfection byproducts in chlorinated water, such as swimming pool water, after trihalomethanes (THMs). Recent research has shown that HAAs levels in the pool water are of interest, since their formation and presence has been linked to cancer. They are highly water-soluble and are toxic to humans and plants. Because of their potential carcinogenotoxity, the U.S. Environmental Protection Agency (U.S. EPA) has reduced the maximum contamination level of some regulated HAAs from 0.060 mg/L to 0.030 mg/L. The World Health Organization (WHO) has also set the qualitative target levels for HAAs at 80 µg/L for dichloroacetic acid and 100 µg/L for trichloroacetic acid. HAAs are generally difficult to determine because of their strong acidic and hydrophilic character. There are nine haloacetic acid congeners that contain chlorine or bromine, five of which are regulated and four unregulated. The regulated HAAs are monochloroacetic acid (MCAA), dichloroacetic acid (DCAA), trichloroacetic acid (TCAA), monobromoacetic acid (MBAA) and dibromoacetic acid (DBAA). The unregulated HAAs are bromochloroacetic acid (BCAA), bromodichloroacetic acid (BDCAA), chlorodibromoacetic acid (CDBAA) and dibromoacetic acid (DBAA). The current U.S. EPA approved methods for HAA analysis are EPA methods 552.1, 552.2 and 6251, all of which involve cumbersome liquid sample preparation, or even derivatization, prior to gas chromatography (GC) analysis.

EPA Method 552 and EPA Standard Method 6251 suffer low detection limits at the cost of inept and lengthy extraction-derivatization procedures. EPA Method 552.1, which employs ion-exchange derivatization followed by GC analysis, would be a better option, as it uses less solvent, but it suffers from an increased detection limit. Typical analysis time for the above methods range from three to four hours, and few analytes are detected. Several researchers have capitalized on the limitations of the U.S. EPA methods to develop alternative techniques. However, most of them still require derivatization prior to GC analysis. Interestingly; due to the ionic nature of HAAs, alternative methods (such as liquid chromatography, ion chromatography, and capillary electrophoresis) that do not require derivatization have been explored with marked success. Electron Spray Ionization-Mass Spectrometry (ESI-MS) provides excellent sensitivity and selectivity, but high cost precludes its widespread use. Detection limits of these methods have been found to be significantly greater than the GC methods. Conventionally, liquid-liquid extraction (LLE) and solid-phase extraction (SPE) are the most common sample preparation techniques for HAA analysis. However, the multistep sample extraction and clean up procedures involved require voluminous solvents, are tedious, time-consuming, and lead to analyte loss. Generally, most current methods used in the determination of HAAs in water matrices suffer greatly from increased time for sample pretreatment and degradation of unstable species. Porous membrane-based liquid phase microextraction (LPME) techniques have been explored for good analyte enrichment properties. However, the solvents available for extracting both polar and semi-polar compounds are limited.

In previous years, a sorbent based solid phase microextraction (SPME) technique has emerged as a promising technique for preconcentration of HAAs, although its success is tempered by drawbacks associated with high cost, fragility, and carry-over effects of the fiber. Recently, a dispersive micro-solid phase extraction with ionic liquid-modified silica for the determination of organophosphate pesticides in water by UPLC-PDA detector was ratified, and it demonstrated the precise and sensitive determination of the target analytes. Micro-solid phase extraction technique has shown great promise, since it is robust, durable and capable of reusability. The device does not suffer from carry-over problems, and is easy to prepare in-house at a reasonable cost. Application of the technique for HAA concentration and separation from aqueous solution would be desirable.

Thus, a micro-solid phase extraction of haloacetic acids solving the aforementioned problems is desired.

SUMMARY OF THE INVENTION

The micro-solid phase extraction of haloacetic acids is a procedure that extracts haloacetic acids from aqueous solution using iron-modified rice husk as the stationary phase or sorbent. Rice husks (RH) provide an excellent source of silica. The sorbent is prepared by incinerating the husks to produce a white powder that is treated with 1.0 M nitric acid for 24 hours, filtered, and then washed with a copious amount of water at pH 5.6 to produce rice husk silica. The silica is washed with base, and then titrated with a 10% $Fe^{3+}$ solution to pH 5, which forms a gel. The gel is aged, filtered, dried, and calcined to produce a nitrate-free iron-modified rice husk sorbent. The sorbent may be packaged in porous, heat-sealed polypropylene membrane envelopes and used for extraction of HAAs from water. The HAA analytes may be desorbed by ultrasonication in methanol for analysis and quantification.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
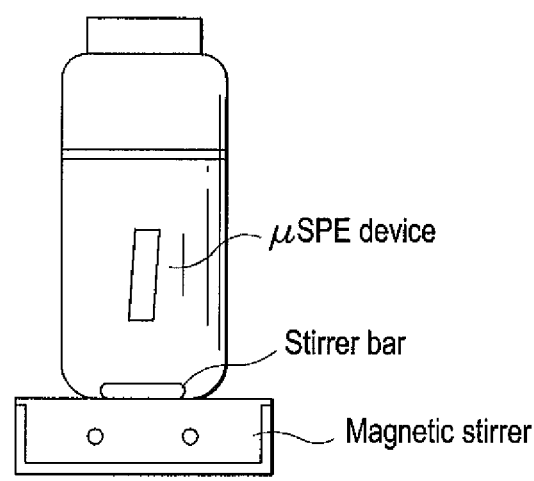
FIG. 1 is schematic diagram of the micro-solid phase extraction (µ-SPE) experimental set up used for testing the µ-SPE technique according to the present invention.

The micro-solid phase extraction of haloacetic acids is a procedure that extracts haloacetic acids from aqueous solution using iron-modified rice husk as the stationary phase or sorbent. The following describes preparation of the sorbent and testing of the micro-solid phase extraction of haloacetic acids.

All the reagents used were of better analytical grade. HPLC grade organic solvents were obtained from Merck (Darmstadt, Germany). Sodium hydroxide, sodium sulfate, hydrochloric acid and sodium dihydrogen phosphate monohydrate ($NaH_2PO_4 \cdot H_2O$) were obtained from J. T. Baker (Philips Burg, N.J.). Orthophosphoric acid (85%) purity was purchased from Carl Erba (Milan, Italy). Ultra-pure water was prepared using Milli-Q (Milford, Mass.) System. The pH of the Milli-Q water was 5.6. A mixture of six HAAs standard solution in methyl tert-butyl ether (MTBE) containing 2000 μg/ml was purchased from Supelco (Supelco Park, Pa., USA). Sulfuric acid (98%, grade for analysis) was obtained from Merck.

Chromatographic analyses were conducted using a Waters Acquity Ultra Performance Liquid Chromatography system (Waters Corporation, Madrid, Spain) using an Acquity UPLC BEH $C_{18}$ column. The mobile phase consisted of A-20% methanol and B-80% 15 mM sodium dihydrogen phosphate buffer solution adjusted to pH 2.0-2.2 at a flow rate of 0.2 mL/min. The separated components were determined using Acquity Photo Diode Array Detector, PDA (Waters Corporation) under double channel system at wavelengths of 210 nm and 220 nm. Empower Software (Waters Corporation) was used for data acquisition and analysis. Polypropylene sheet membrane (157 μm thickness and 0.2 μm pore size) was purchased from Membrana (Wuppertal, Germany). Various sorbents, including C-18, Graphitic, Carbon-nanotubes, HayeSepA (divinylbenzene ethyleneglycoldimethylacrylate (DVB/EGDM)), and Porapak R (divinylbenzene/vinylpyrrolidinone) were obtained from Alltech (Deerfield, Mich.). RH were obtained from a rice mill in India. Plastic crimper vials of 0.2 ml capacity were secured from Landgraaf bioplastics industry in the Netherlands and were used in desorbing our target analytes by ultra-sonication.

A working stock solution (2000 mg $L^{-1}$) of HAAs was prepared using HPLC grade methanol in a 10 ml volumetric flask and stored at 4° C. for subsequent usage. The samples of required concentration were prepared by diluting the stock solution of HAAs to respective concentrations. Wide ranges of calibration standard (1.0-150 μg/L) were prepared by spiking to different aliquots of 20 ml ultra-pure water maintained at a pH of 4.0. Extraction was carried out on these samples.

Example 1

Preparation of Iron-Modified Rice Husk Sorbent (Silica-Fe)

Rice husk waste was modified to silica-Fe using the sol-gel process. Rice husks RH were washed with a plenteous amount of distilled water. The cleaned sample was then air-dried and incinerated at a temperature of 700° C. in a muffle furnace for 6 hours to form a white powder. The powder was treated with 1.0 M $HNO_3$ for 24 h, filtered, and washed with deionized water until a pH value of 5.6 was obtained to form rice husk silica. The silica was oven-dried at 110° C. overnight. About 5.0 g of RHA was added to 250 ml of 6.0 M NaOH, stirred for 12 h, and filtered to remove un-dissolved material. 3.6 g of cetyltrimethylammonium bromide was added into the resultant sodium silicate solution and stirred until complete dissolution. The filtrate was titrated with 10% $Fe^{3+}$ solution [3.62 g Fe $(NO_3)_3 \cdot 9H_2O$ dissolved in 200 ml of 3.0 M $HNO_3$] until pH 8 was reached. Drop-by-drop titration followed until pH 5 was finally obtained. The gel formed was then aged for 5 days, after which it was filtered through suction filtration and washed with distilled water. Finally, the product was oven-dried at 110° C. for a day, and then calcined at 500° C. for 6 h to produce the nitrate-free silica-Fe of interest. Incorporation of Fe (III) into the silica porous structure improves the adsorption capacity and selectivity for HAAs through electrostatic interactions.

Example 2

Preparation of μ-SPE Extraction Device

The porous polypropene membrane serves as a filtering device and prevents particulates and humic substances from complex sample matrices adsorbing on the sorbent. This improves the sensitivity of the extraction. The membrane envelope was made from two overlapping sheets whose open edges were heat-sealed. One of the two open ends was then heat sealed. A cut glass tube was used to introduce 20 mg of sorbent material through the remaining open end, which was later heat sealed to secure the contents in a 1.5 by 0.5 cm. dimension envelope. After successful packaging, the device was reweighed to ensure consistency in weight measurements. Each prepared device was conditioned in acetone for 10 minutes, dried, and then placed in 20 mL of ultrapure water in a glass vial containing a magnetic stirring bar. Without adjusting pH, temperature and salt concentration, the water sample was agitated on a vortex at a stirring speed of 700 rpm for 20 minutes to allow extraction to take place. After extraction, using a pair of tweezers, the μ-SPE device was removed and then fitted into a 2004 crimper vial for solvent desorption. Methanol was then used as a desorption solvent after which 5 μL of the extract was directly injected in to UPLC for analysis. FIG. 1 shows the experimental setup of the μ-SPE extraction device.

The micro-solid phase extraction method provides reduced sample preparation steps, and improved selectivity and sensitivity towards HAA analysis in a water matrix. Halo acetic acids are relatively polar, non-volatile, and water-soluble species. The method was first validated by optimizing the extraction conditions to enhance recovery of the analytes. The analysis was done in triplicate by spiking measured water samples with known concentrations of HAA standards. The parameters that were investigated include extraction time, desorption volume, and suitability of the sorbent. A dilution volume of 20 ml was chosen at the start.

Figure 2:
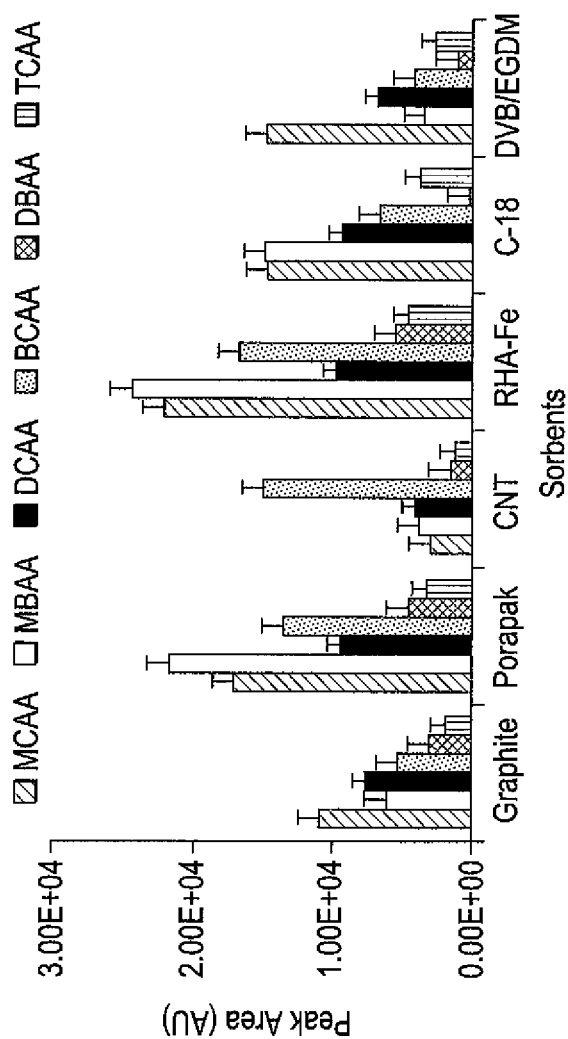
FIG. 2 is a chart showing a comparison of the effectiveness of various sorbents for the µ-SPE extraction of (haloacetic acids) HAAs in spiked water samples (n=3).

The efficiency of the μ-SPE device depends mainly on the nature of the sorbent material used. For comparative analysis, six different materials, including C-18, Graphitic carbon, Carbon-nanotubes, HayeSepA (divinylbenzene ethyleneglycoldimethylacrylate (DVB/EGDM)), Porapak R (divinylbenzene/vinylpyrrolidinone), and RHA-Fe were evaluated. After extraction, the extraction device was desorbed in methanol. The results are represented in FIG. 2. The mechanism of μ-SPE is similar to the conventional SPE method. Compared to other materials, silica-Fe shows higher extraction efficiency towards HAAs. The amorphous silica and iron (iii) ions in RH silica were considered as the key materials for the adsorption of HAAs.

Selection of desorption volume was done for all sorbents using methanol as a desorption solvent. Varying methanol volumes, ranging from 100 μl to 300 μl, were evaluated. Results were as anticipated, as the lower volume gave higher peak areas. A volume of 150 μl was, however, found to be the optimum volume for all sorbents.

Figure 3:
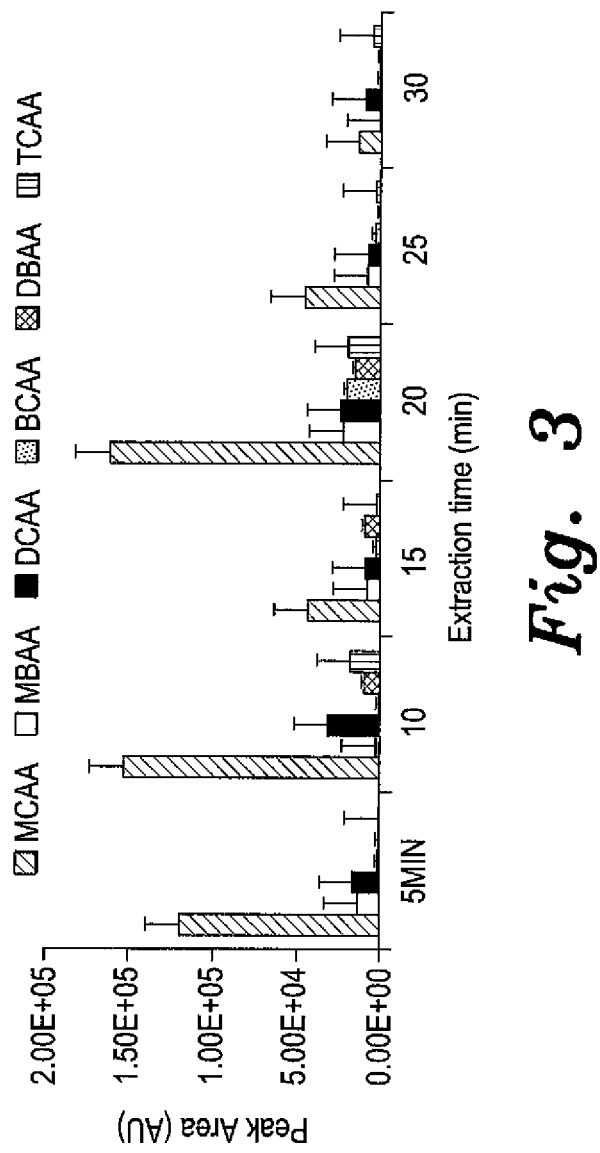
FIG. 3 is a chart showing the extraction of HAAs by micro-solid phase extraction according to the present invention as a function of time.

In the μ-SPE method, the amount of analyte extracted depends on rate of its mass transfer from the water sample to the solid sorbent phase enclosed within the device. Sample agitation helps during the extraction, since the extraction efficiency is improved. This is because the contact between the analyte and the extractant is enhanced. For this reason the effect of extraction (agitation) time using a vortex was evaluated for a range of 5 minutes to 30 minutes. From the chart shown in FIG. 3, twenty minutes of vortex extraction was considered to be the optimum value. After the first extraction, the device was tested for carry-over effects by desorbing it in methanol for a second time. No meaningful peaks were realized. This meant the µ-SPE device was reusable after careful washing in acetone.

The repeated use of the device was henceforth evaluated, and the results showed that it could be used for more than 20 extractions. This further proved the robustness of our device and it was noted that its effectiveness depends on the durability of the protective membrane.

The present µ-SPE method was tested on swimming pool water taken from two swimming pools around King Fahd University of Petroleum and Minerals in Dhahran, Saudi Arabia. Table 1 shows the mean concentration obtained for the six HAA analytes. The µ-SPE method was able to determine the HAAs analytes at ng/L levels, and their contamination levels were far below the standard value set by USEPA of 0.03 mg/L.

TABLE 1

Mean HAA Concentrations in Two KFUPM Swimming Pools

| Analyte | Mean Conc. (ng/l)* Pool A | Mean Conc. (ng/l)* Pool B |
|---|---|---|
| MCAA | 46.5 | 48.6 |
| MBAA | 24.6 | 8.6 |
| DCAA | 34.6 | 11.3 |
| BCAA | 6.8 | 4.1 |
| DBAA | 16.2 | 16.4 |
| TCAA | 12.6 | none detected |

*RSDs range from 2%-7%

Membrane-protected micro-solid phase extraction followed by UPLC-UV analysis was developed to determine HAAs in swimming pool waters. It was a simple, sensitive, and relatively fast technique that did not require any derivatization. The target analytes were directly analyzed within ten minutes of UPLC run time. The developed method exhibited good precision and the detection limits were comparable to those of the standard U.S. EPA methods.

The µ-SPE device used in the present invention is easy to make, inexpensive, uses a few microliters of organic solvents, and does not suffer from sample carry-over problems. Each device can be used for more than twenty extraction times, and moreover, the silica-Fe sorbent used is efficient and easy to process.

It is to be understood that the present invention is not limited to the embodiments described above, but encompasses any and all embodiments within the scope of the following claims.

We claim:

1. A method of extracting haloacetic acids from aqueous solution, comprising the steps of:
   preparing a sorbent consisting of porous rice husk silica having particles of iron embedded in the pores, wherein said step of preparing the sorbent comprises the steps of:
   incinerating rice husks to produce a powder;
   treating the powder with 1.0 M nitric acid for 24 hours to produce rice husk silica;
   washing the silica with base to form a sodium silicate solution;
   adding 3.6 g of cetyltrimethylammonium bromide into the sodium silicate solution and stirring until the cetyltrimethylammonium bromide is completely dissolved;
   titrating the silicate solution with a 10% $Fe^{3+}$ solution to pH 5, thereby forming a gel;
   aging the gel; and
   filtering, drying, and calcining the aged gel to produce a nitrate-free, iron-modified rice husk silica sorbent;
   sealing the sorbent in a membrane envelope formed from at least one porous polypropylene membrane to form a packaged sorbent; and
   using the packaged sorbent as the stationary phase for micro-solid phase extraction of the haloacetic acids from the aqueous solution, wherein the membrane envelope provides filtering for preventing particulates and humic substances from complex sample matrices adsorbing on the sorbent.

2. The method of extracting haloacetic acids from aqueous solution according to claim 1, further comprising the step of desorbing the haloacetic acids from the sorbent using a solvent via ultrasonication.

* * * * *